(12) United States Patent
Brown et al.

(10) Patent No.: US 10,925,960 B2
(45) Date of Patent: Feb. 23, 2021

(54) ANTIGEN DELIVERY SYSTEM

(71) Applicant: SRI INTERNATIONAL, Menlo Park, CA (US)

(72) Inventors: Kathlynn C. Brown, Menlo Park, CA (US); Benjamin J. Umlauf, Menlo Park, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 49 days.

(21) Appl. No.: 15/626,075

(22) Filed: Jun. 17, 2017

(65) Prior Publication Data
US 2017/0281752 A1    Oct. 5, 2017

Related U.S. Application Data

(63) Continuation of application No. PCT/US2015/066519, filed on Dec. 17, 2015.

(60) Provisional application No. 62/093,285, filed on Dec. 17, 2014.

(51) Int. Cl.
| | |
|---|---|
| A61K 39/285 | (2006.01) |
| A61K 9/127 | (2006.01) |
| A61K 39/165 | (2006.01) |
| C12N 7/00 | (2006.01) |
| A61K 39/00 | (2006.01) |

(52) U.S. Cl.
CPC .......... *A61K 39/285* (2013.01); *A61K 9/1271* (2013.01); *A61K 39/165* (2013.01); *C12N 7/00* (2013.01); *A61K 2039/55555* (2013.01); *A61K 2039/585* (2013.01); *A61K 2039/605* (2013.01); *C12N 2710/24134* (2013.01); *C12N 2760/18434* (2013.01)

(58) Field of Classification Search
CPC .................................................. A61K 39/285
USPC ..................................................... 424/130.1
See application file for complete search history.

(56) References Cited

U.S. PATENT DOCUMENTS

| | | |
|---|---|---|
| 2013/0164364 A1 | 6/2013 | Paulson et al. |
| 2014/0271827 A1 | 9/2014 | Irvine et al. |

FOREIGN PATENT DOCUMENTS

| | | |
|---|---|---|
| AU | 2015364447 | 12/2015 |
| AU | 2015364447 A1 | 7/2017 |
| CA | 2971408 | 12/2015 |
| CA | 2971408 A1 | 6/2016 |
| CN | 102066410 A | 5/2011 |
| CN | 201580075499.5 | 12/2015 |
| CN | 107223051 A | 9/2017 |
| EP | 2127670 A1 | 12/2009 |
| EP | 15871129.1 | 12/2015 |
| EP | 3226840 A1 | 10/2017 |
| IL | 252972 | 12/2015 |
| IN | 201717023078 | 12/2015 |
| JP | 2014519496 A | 8/2014 |
| JP | 2017-532946 | 12/2015 |
| JP | 2017538754 A | 12/2017 |
| KR | 10-2017-7019331 | 12/2015 |
| KR | 20170093970 A | 8/2017 |
| WO | WO-98/33520 A1 | 8/1998 |
| WO | WO-2008/105174 A1 | 9/2008 |
| WO | WO-2012/018377 A2 | 2/2012 |
| WO | PCT/US2015/66519 | 12/2015 |
| WO | WO-2016/100748 A1 | 6/2016 |

OTHER PUBLICATIONS

Weidanz et al (J Immunol, 2006, 177: 5088-5097).*
Ogg et al (British Journal of Cancer, 2000, 82(5): 1058-1062).*
Denkberg et al (J Immunol, 2003, 171: 2197-2207).*
Ota et al., Hemagglutinin Protein Is a Primary Target of the Measles Virus-Specific HLA-A2,-Restricted CDS+ T Cell Response during Measles and after Vaccination. J Infect Dis. 2007, vol. 195{12), p. 1799-1807.
Umlauf et al., Identification of a Novel Lysosomal Trafficking Peptide using Phage Display, Biopanning Coupled with Endocytic Selection Pressure. Bioconjug Chem. Oct. 2014, vol. 25{10), p. 829-837.
ISR-WO PCT/US15/66519.
Office Action dated May 31, 2018 by the Canadian Patent Office for CA Application No. 2,971,408, which was filed on Dec. 17, 2015 and published as CA 2,971,408 on Jun. 23, 2016 (Applicant—SRI International) (6 pages).
Nag, et al., "Surface Engineering of Liposomes for Stealth Behavior". Pharmaceutics. (2013), vol. 5(4), p. 542-569.
Belogurov, Jr., et al., Liposome-encapsulated peptides protect against experimental allergic encephalitis. FASEB J. (2013), vol. 27(1), p. 222-231.
Colletier, et al., Protein encapsulation in liposomes: efficiency depends on interactions between protein and phospholipid bilayer. BMC Biotechnol. 2002, vol. 2:9. (8 pages).
Umlauf, B.J. et al., Modular Three-component Delivery System Facilitates HLA Class I Antigen Presentation and CD8+T-cell Activation Against Tumors. Mol Ther. 2015; 23(6):1092-102.
Wei, M. et al., Hepatocellular Carcinoma Targeting Effect of PEGylated Liposomes Modified with Lactoferrin. Eur J Pharm Sci. 2012; 46(3):131-41.
Supplementary European Search Report dated Nov. 15, 2017 by the European Patent Office for Patent Application No. 15871129.1, which was filed on Dec. 17, 2015 and published as EP 3226840 on Oct. 11, 2017 (Inventor—Brown et al.; Applicant—SRI International;) (9 pages).
International Preliminary Report on Patentability dated Jun. 20, 2017 by the International Searching Authority for Patent Application No. PCT/US2015/66519, which was filed on Dec. 17, 2015 and published as WO 2016/100748 on Jun. 23, 2016 (Inventor—Brown et al.; Applicant—SRI International;) (9 pages).

(Continued)

*Primary Examiner* — Sean E Aeder
(74) *Attorney, Agent, or Firm* — Ballard Spahr LLP

(57) ABSTRACT

A minimal antigen delivery system consists essentially of PEGylated stealth liposomes loaded with an immunogenic human leukocyte antigen (HLA) class restricted peptide and surface modified with a cell targeting peptide which mediates binding and internalization of the liposomes into a target cell.

16 Claims, No Drawings

(56) References Cited

OTHER PUBLICATIONS

Ogg et al. "Sensitization of tumour cells to lysis by virus-specific CTL using antibody-targeted MHC class I/peptide complexes" Br J Cancer. Mar. 2000;82(5):1058-62.
Weidanz et al., Levels of specific peptide-HLA class I complex predicts tumor cell susceptibility to CTL killing, J Immunol. Oct. 15, 2006;177(8):5088-97.
Notice of Reasons for Refusal dated Oct. 8, 2019 by the Japanese Patent Office for JP Application No. 2017-532946, filed on Dec. 17, 2015 and published as 2017-538754 on Dec. 28, 2017 (Applicant—SRI International) (Translation—4 Pages).
Office Action dated Nov. 7, 2019 by the SIPO for CN Application No. 201580075499.5, filed on Dec. 17, 2015 and published as CN107223051A on Sep. 29, 2017 (Applicant—SRI International) (Translation—8 Pages).
Notice of Rejection dated May 13, 2019 by the Japanese Patent Office for JP Application No. 2017-532946, filed on Dec. 17, 2015 and published as 2017-538754 on Dec. 28, 2017 (Applicant—SRI International) (Translation—3 Pages).

\* cited by examiner

ANTIGEN DELIVERY SYSTEM

This application is a continuation of PCT/US15/66519; filed Dec. 17, 2015, which claims priority to Ser. No. 62/093,285; filed Dec. 17, 2014.

This invention was made with government support under grant number RO1CA164447 awarded by the National Cancer Institute of the National Institutes of Health, and under grant number 146339 awarded by the National Science Foundation Graduate Research Fellowship. The government has certain rights in this invention

INTRODUCTION

Cell-mediated (CM) immunotherapies for cancer treatment are designed to activate the body's adaptive immune responses against a malignant growth (1,2). Generally, the goal of a CM response is to activate a cytotoxic T-cell response against a tumor to eliminate cancer cells. The principle of these treatments is straightforward, yet current work studying the complexity of the tumor micro-environment (2,3) as well as methods that attempt to directly activate T cells against tumor antigens (4-6) demonstrate the difficulty associated generating an immune response against a tumor.

Several CM cancer immunotherapies exist today, including PD-1 inhibitors, injection of live virus or viral particles into tumors, and adoptive T-cell therapies (1,6-8). However, concerns regarding efficacy, safety, and/or cost have limited the use of many of these treatments. To address these concerns, we sought to develop a novel treatment based on developing a fully synthetic, minimal delivery system that facilitates presentation of human leukocyte antigen (HLA) class I restricted immunogenic peptides specifically on cancer cells without using live virus, viral subunits, or biologically derived material.

Based on these requirements, we developed a liposomal based agent consisting of a neutral, stealth liposome that encapsulates a synthetically manufactured immunogenic HLA class I restricted peptide. In addition, the liposome has a targeting peptide on the external surface that both specifically accumulates in cancer cells and facilitates presentation of the immunogenic peptide in HLA class I molecules. Thus, this treatment is designed to generate a secondary CM immune response specifically against the tumor.

SUMMARY OF THE INVENTION

The invention provides a nanoparticle delivery system that facilitates presentation of an immunogenic measles antigen specifically in cancer cells. The delivery system does not contain viral particles, toxins, or biologically derived material. Treatment with this system facilitates activation of a secondary immune response against cancer cells, bypassing the need to identify tumor-associated antigens or educate the immune system through a primary immune response. The delivery system is a three part modular vehicle, requiring only a stealth liposome displaying a cancer-specific targeting peptide on its exterior surface and encapsulating an immunogenic human leukocyte antigen class 1 restricted peptide. This targeted-nanoparticle facilitates presentation of the peptide in major histocompatibility complex class I molecules. Activation is dependent on the targeting peptide, previous antigen exposure, and utilizes a novel autophagy-mediated mechanism to facilitate presentation. Treatment with this liposome results in a significant reduction of tumor growth using an aggressive LLC1 model in vaccinated C57BL/6 mice. We demonstrate proof-of-principle for a novel cell-mediated immunotherapy that is scalable, contains no biologically derived material, and is an efficacious cancer therapy.

The invention provides a minimal antigen delivery system consisting essentially of PEGylated stealth liposomes loaded with an immunogenic human leukocyte antigen (HLA) class 1 restricted peptide and surface-modified with a cell targeting peptide which mediates binding and internalization of the liposomes into a target cell. Hence, the systems consist or consist essentially of (exclude any additional components that would materially affect the basic and novel operability and function of the system) and/or requires, functionally depends upon, or includes no more than the three recited components: the stealth liposome, targeting peptide and HLA class 1 restricted peptide.

The system is modular and applicable to alternative targeting and/or immunogenic peptides. A wide variety of cell targeting peptides are known in the art, and suitable peptides for targeting any of a variety of cells types are readily selected, such as described herein, wherein preferred target cells are pathogenic, such as cancer cells. Similarly, a wide variety of immunogenic peptides are known in the art, and suitable peptides of alternative HLA types and immunity/vaccination dependencies are readily selected, such as described herein. HLA typing is standardized in clinical practice, and alternative immunized (naturally or vaccinated) populations are readily identifiable; for example, we have similarly tested and validated an antigen derived from the smallpox virus (H-2Kd-restricted vaccinia-specific peptide, A5275-83, VACV-A52).

In exemplified embodiments, the HLA class 1 restricted peptide is measles virus hemagglutinin peptide H250, and/or the cell-targeting peptide is a cancer cell targeting peptide that is H1299.3.

The invention also provides methods of making the subject antigen delivery systems, comprising the step(s) of: loading the PEGylated stealth liposomes by forming the liposomes in the presence of the class-1 restricted peptide; and/or surface modifying the PEGylated stealth liposomes loaded with the HLA class restricted peptide by conjugating to the surface the cell targeting peptide.

The invention also provides methods of using the subject antigen delivery systems, comprising the step(s) of: introducing the antigen delivery system into a host in need thereof, and/or detecting a resultant immune response or inhibition of the target cell.

The invention specifically provides all combinations of the recited embodiments, as if each had been laboriously individually set forth.

DETAILED DESCRIPTION OF PARTICULAR EMBODIMENTS AND EXAMPLES THEREOF

In this proof-of-concept study, we synthesized a liposome that encapsulates H250 (1), an immunogenic HLA class 1 restricted peptide identified from measles hemagglutinin protein. The liposome is designed to specifically internalize in cancer cells by displaying the targeting peptide H1299.3 on the exterior surface (10). H1299.3 is a 20mer, cancer-specific targeting peptide identified using a novel phage display technique that allows for selection of cancer-specific targeting peptides that preferentially internalize in cancer cells via a defined mechanism of endocytosis. This peptide was dimerized on a lysine core and is fully functional outside the context of the phage particle. The H1299.3 peptide accumulates specifically in a panel of non-small cell lung cancer (NSCLC) cell lines compared to a normal bronchial epithelial cell control cell line via a clathrin-dependent mechanism of endocytosis. In this study, we demonstrate that H1299.3 facilitates functional presentation of an immunogenic antigen in both major histocompatibility complex (MHC) and HLA class I molecules as indicated by CD8+-specific interferon (IFN)γ secretion. In addition, H1299.3 facilitated presentation utilizes an autophagy-dependent mechanism. Finally, treatment with H1299.3 targeted liposomes containing H250 substantially reduces the growth rate of sub-cutaneous LLC1 tumors implanted in vaccinated C57BL/16 mice compared to treatment with vehicle control.

Generating a targeted liposome for viral-antigen presentation specifically in cancer cells. The first goal of this study is to create a synthetic delivery system that is suitable for specific delivery of antigenic cargo into cancer cells. The vehicle needs to have high payload capacity and shield the immunogenic peptide cargo without modification as presentation in HLA class I molecules is restricted by size and position of amino acid residues (11). Therefore, we decided to utilize liposomes. Liposomes are readily manufactured from synthetic material, easily loaded with synthetic peptide, and amenable to modification with targeting ligands (12). Further, liposomes accumulate passively in tumors based on the enhanced permeability and retention effect, potentially enhancing the specificity of the treatment (13). We manufactured 100-nm stealth liposomes that encapsulate a synthetically manufactured 9mer immunogenic peptide, H250 with a loading efficiency of approximately 60%. DSPE PEG2000 modified with maleimide is incorporated into the lipid formulation to allow for conjugation of a thiol containing targeting ligand to the liposome (12).

The H1299.3 targeting ligand specifically accumulates in cancer and facilitates HLA class I presentation. In order to quantify the ability of the liposomal formulation to facilitate presentation of H250 immunogenic peptide, we first needed to develop a system to determine if H250 is present in the cleft of HLA class I molecules. H250 is an immunogenic peptide identified from sequencing peptides present in HLA A*0201 molecules following measles infection (1) Thus, we identified peripheral blood mononuclear cells (PBMCs) from anonymous donors that were HLA A*02 positive, and determined if these donors were vaccinated against measles by culturing donor PBMCs with free H250 peptide and measuring IFNγ secretion. We successfully identified two donors that were HLA A*02 positive and had previously been vaccinated against measles virus. PBMCs from these two donors, D4 and D9, were used in the subsequent assays to identify and characterize a cancer-specific targeting peptide that can facilitate HLA class 1 presentation. Similarly, an appropriate cancer cell line was needed to serve as the antigen-presenting cells. For this, we utilized the human NSCLC cell line, H1993, which we determined to be HLA A*02 positive.

Next, we screened known cancer-specific targeting peptides to identify a targeting peptide that can facilitate presentation of H250 from the targeted liposomal formulation in HLA class I on the external surface of the cell. Panels of cancer targeting peptides have been identified by our group and others; therefore, we identified three different cancer-specific targeting peptides that internalize into H1993 that have been previously published: H1299.2, H2009.1, and H1299.3. Each of these peptides specifically internalize in NSCLC cell lines compared to normal bronchial epithelial cells (14). The peptides were conjugated to the surface of the liposome by a thiol-ester linkage resulting from a Michael addition of a single sulhydryl group on the targeting peptide to the maleimide present on the liposome. A peptide that does not internalize into H1993 cells, H460.1, was utilized a control (14).

To screen each targeting peptide, H1993 cells were treated with H1299.2, H2009.1, H460.1, or H1299.3 targeted liposomes containing H250 for 3 hours. The cells were then washed to eliminate noninternalized/bound liposomes and then cocultured with donor PBMCs for 72 hours. Cell culture supernatants were harvested and analyzed for IFNγ secretion via enzyme-linked immunosorbent assay (ELISA) as a measure of T-cell activation. Free H250 peptide served as a positive control in this assay. Only the H1299.3-targeted liposomes containing H250 resulted in a significant increase in IFNγ (Quench) and compared to the H1299.3 targeted liposomes containing H250 (H1299.3). Treated H1993 cells were cocultured with donor PBMC as described above. Once again, only H1299.3-targeted liposomes containing H250 resulted in a significant increase in IFNγ secretion. These data provide further support that presentation is dependent on both the H250 antigenic peptide and H1299.3 targeting peptide. These results were duplicated using a second PBMC donor, D9, demonstrating presentation is not patient specific. Depleting CD8+ T cells from the PBMC cultures results in loss of IFNγ secretion in both human samples. These data indicate that H250 is present in HLA class I molecules and the H1299.3-targeted liposomes containing H250 facilitate the activation of a CD8+ memory T-cell response in individuals previously vaccinated against measles.

To further characterize the immune response generated by this treatment, we quantified the levels of secreted TNFα in coculture supernatants. Similar to the above mentioned data, we observed a significant increase in TNFα secretion in H1993 cells treated with H1299.3-targeted liposomes containing H250 relative to H1993 cells treated with blank liposomes in both human donors. Upon CD8+ depletion, a reduction in TNFα secretion is observed following treatment of H1993 cells with H1299.3 targeted liposomes containing H250.

To extend the breadth of these studies, we identified a marine lung cancer cell line derived from C57BL/6 mice, Lewis Lung Carcinoma 1 (LLC1) that internalizes the H1299.3 targeting peptide. We then generated murine CD8+ cells with TCR that recognizes MHC class I loaded H250 (1) by vaccinating C57BL/6 mice with an extended version of H250 and subsequently harvesting lymphocytes as a source of CD8+ T cells. LLC1 cells were treated with control or H1299.3-targeted liposomes containing H250, washed, and then incubated. Depleting CD8+ T cells from the lymphocyte pool resulted in significant loss of IFNγ secretion similar to the human data. Thus, the H1299.3-targeted liposome system is able to deliver H250 for functional presentation in both MHC and HLA class I molecules.

H1299.3 facilitated HLA class I presentation requires autophagy. To determine the mechanism by which H1299.3 facilitates presentation of H250 in HLA class I molecules, we characterized the subcellular accumulation of the H1299.3 peptide. Previous data indicated the newly identified H1299.3 peptide colocalizes with Lamp-1 (10) whereas the other cancer-specific targeting ligands H1299.2 and H2009.1 accumulate in perinuclear regions (14). Therefore, we reasoned that the subcellular trafficking pattern is crucial to H1299.3 facilitated presentation (14). Similar to previous results, H1299.3 and Lamp-1 colocalize in both H1993 and LLC1 cell lines as determined by live cell laser scanning confocal microscopy. However, these data do not offer a clear explanation for mechanism of presentation. Lamp 1 is a marker of both lysosomes and autolysosomes (15) raising the possibility that autophagy plays a role in this process. To test this hypothesis, the imaging experiments were repeated using LLC1 and H1993 cells that contain a GFP-LC3B construct which is a marker for autophagosomes. Clear colocalization with LC3B puncti is observed in both cell lines indicating H1299.3 accumulates autolysomes. Importantly, treatment of the corresponding cells with a scrambled sequence version of H1299.3 results in no significant peptide internalization and consequently, no co-localization with either Lamp-1 or LC3B. Together, the data show sequence-dependent colocalization of the H1299.3 peptide in autophagosomes.

If H1299.3 accumulates in autophagic vesicles, perturbing autophagy should result in loss of H250 presentation in MHC class I molecules following treatment with H1299.3-targeted liposomes. LLC1 cells were treated with H1299.3-targeted liposomes containing H250 in the presence of the inhibitors, chloroquine, with mouse lymphocytes in a similar manner to the human coculture assay presented above. Similar to the human data, treatment with H1299.3-targeted liposomes containing H250 resulted in a significant increase in IFNγ secretion compared to controls chlorpromazine, nystatin, and wortmannin. After allowing trafficking of the peptides to occur, the LLC1 cells were fixed and cocultured with lymphocytes as previously described. Treatment with known inhibitors of autophagy, including wortmannin and chloroquine, resulted in significant reduction in IFNγ secretion compared to controls. Chlorpromazine, an inhibitor of clathrin-mediated endocytosis, reduced presentation. This is consistent with our previous results demonstrating that the H1299.3 peptide is internalized by a clathrin-mediated mechanism, and cellular uptake of the peptide is reduced in the presence of chlorpromazine (10). Nystatin, an inhibitor of cholesterol-dependent endocytosis exhibits no effect.

To further validate the role of autophagy in H1299.3 facilitated presentation, LLC1 cells were treated with siRNA targeting autophagy-related protein 7 (ATG7). ATG7-specific knockdown in LLC1 cells by siRNA is quantified via western blot using β-actin as loading control. Treatment with ATG7-specific oligos resulted in ~80% reduction in ATG7 protein levels whereas minimal decrease in ATG7 levels are observed using a control siRNA hairpin (16) Knockdown of ATG7 significantly reduced IFNγ secretion in LLC1 cells incubated with H1299.3 targeting liposomes containing H250 compared to LLC1 cells not treated with siRNA or LLC1 cells treated control siRNA. We repeated ATG7 knockdown assays in H1993 cells. Similar to LLC1 cells, we observed ~80% reduction in ATG7 protein levels in H1993 cells treated with siRNA oligos targeting ATG7 via western blot. Treatment with control siRNA did not affect ATG7 levels. ATG7 knockdown in H1993 cells resulted a significant decrease in IFNγ secretion following treatment with H1299.3-targeted liposomes containing H250 and coculture with D9 PBMCs compared to controls. Thus, the microscopy and phenotype data imply that H1299.3 facilitates presentation of H250 via an autophagy-dependent mechanism.

H1299.3-targeted liposomes encapsulating H250 reduce tumor burden in vivo. Next we utilized H1299.3-targeted liposomes containing H250 in a murine model to determine efficacy of this platform as a CM immunotherapy. C57BL/6 mice were vaccinated against H250 then LLC1 cells were implanted subcutaneously into the hind flank. LLC1 tumors were grown until palpable (~150 mm$^3$) at which point mice were treated six times intravenously (I. V.) with H1299.3-targeted liposomes containing H250 or vehicle that lacked the H250 immunogenic peptide. We observed a significant decrease in LLC1 tumor growth rate in the treated group following the third treatment. After explanting the tumors, we observed >2-fold reduction in tumor weight and volume.

During the tumor efficacy studies, no significant difference in animal weight is observed between groups, and the animals demonstrate no weight loss. Together, these data indicate that the animals suffer no gross toxicity from the treatment. None-the-less, liposomes are cleared via the liver raising the possibility of liver toxicity. As such, we quantified serum levels of AST and ALT in nonvaccinated mice containing subcutaneous LLC1 tumors following three treatments with either H1299.3-targeted liposomes containing H250 or vehicle control. All values are within normal ranges indicting limited liver toxicity. Further, liver, kidney, heart, and lung tissues were harvested, sectioned, and stained with H&E. Sections from these organs identified no gross abnormalities in either the treated or vehicle groups.

Finally, to connect the in vitro data to the in vivo data, tumors were sectioned and stained for CD8+ cells. A 10-fold increase of CD8+ cells is observed in tumors treated with H1299.3-targeted liposomes compared to vehicle-treated tumors consistent with the in vitro data demonstrating a CD8+ T-cell response. To further support that the H1299.3-targeted liposome delivers H250 in vivo, nonvaccinated mice containing subcutaneous LLC1 tumors were treated three times with either H1299.3-targeted liposomes containing H250 or vehicle control. The tumor and liver tissues from these mice were then harvested and single cell suspensions of tumor cells and hepatocytes were generated. These primary cells were directly utilized as antigen-presenting cells (APCs) in the coculture assays outlined above using lymphocytes from vaccinated. C57BL/6 mice. Tumor cells treated with H1299.3-targeted liposomes containing H250 induced a significant increase in IFNγ secretion compared to vehicle-treated tumor cells. Thus, the H1299.3 liposomal formulation is able to deliver H250 to tumors and the H250 peptide is presented in MHC class I molecules on the tumor in vivo. By comparison, using the hepatocytes as the APC, there was no difference in IFNγ secretion levels in either group. Thus, even if the liposomes accumulate in the liver, H250 is not presented in MHC class I as measured by the lack CM immune response generated against the liver cells. In sum, these data imply treatment with H1299.3-targeted liposomes containing H250 is nontoxic and H1299.3 can facilitate presentation of H250 preferentially in a tumor in vivo.

We present a novel cancer immunotherapy based on developing a minimal delivery system to facilitate presentation of HLA class 1 restricted immunogenic peptide in cancer cells, resulting in a secondary immune response against a tumor. This approach bypasses the need to identify tumor-associated antigens or to generate a primary immune response against the tumor, which are major hurdles in cancer vaccine development. Unlike immunomodulators, the immune response generated by our liposomal delivery approach is antigen specific and does not involve an overall general activation of the immune response. This minimizes problems with autoimmune and off-target effects. This protocol also differs from current virus-based immunotherapies, as viral products or live viruses are not employed, reducing safety concerns associated with these types of therapies. A potential downside with our approach is that it is unlikely to generate inflammatory conditions that occur with viral infections, potentially reducing the potency of the immune response. In part, this problem is mitigated by utilizing a secondary immune response that requires less inflammatory inputs to generate an immune response. Furthermore, evidence exists that the tumor microenvironment exhibit inflammatory conditions in which case our therapy maybe using this condition for cytokine inputs (3).

Utilizing a delivery ligand to facilitate HLA class I presentation has previously been achieved using Cholera or Shiga toxins fused to class 1 restricted immunogenic peptides (17-19). Yet, these toxins accumulate indiscriminately in cells and are not targeted specifically to cancer cells. H1299.3 selectively accumulates in cancer cells and demonstrates limited binding to normal human bronchial epithelial cells thus potentially providing a greater therapeutic treatment window (20,21).

Furthermore, manufacturing Cholera or Shiga toxin requires biological synthesis and concerns remain about immunogenicity of the toxin-carriers. In addition, this work differs from hapten painting or antibody-recruiting strategies in which a targeting agent delivers a hapten to the cell surface, resulting in antibody recruitment. The therapy presented in this manuscript is designed to directly activate T cells by specific presentation of HLA class I restricted antigens in cancer cells via an internalization mechanism rather than generating antibody-dependent cellular cytotoxicity from hapten immobilization on the cell surface.22,23.

H1299.3 utilizes an autophagy-dependent mechanism to facilitate presentation of immunogenic peptides. Coupled with previous data, H1299.3 appears to internalize via clathrin-mediated endocytosis and traffic to lysosomes or autolysosomes. Autophagy is appreciated to be involved in classical class II presentation but its role in class I antigen presentation is still emerging. Our data here along with recent reports indicate that autophagy can also participate in class I presentation (24,25). We hypothesize that H250 peptide is recycled back into the cytosol along with contents of the autolysosome thereby allowing for transport by TAP into the ER and subsequent presentation (15,26).

Multiple subcellular locations feed into the HLA class I path-way including cytosol, endoplasmic reticulum, and secretory network. Of note, the previously mentioned Cholera toxin B presentation strategy uses the Golgi secretory network (20,27). This implies that ligands which traffic to multiple subcellular location maybe suitable for use in this CM immunotherapy. However, our data indicate that the immunogenic peptide needs to feed into the HLA class I presentation pathway to be effective. Case in point, other NSCLC-targeting peptides that bind to and are internalized into H1993 cells did not facilitate presentation (14).

These peptides accumulate and remain sequestered in a perinuclear compartment; thus intracellular delivery of the antigenic peptide does not necessarily result in presentation of the antigen. This treatment is designed to elicit a secondary immune response that allows for a more rapid and potentially efficacious immune response against the tumor. However, it also necessitates that the therapy is both HLA type and vaccination status dependent (1,28). HLA typing is standardized in clinical practice; however, immunogenic peptides that bind to different HLA types will need to be identified. In addition, although ~95% of the United States is vaccinated against measles for many patients that may have been years ago implying the need to quantitate immune response to measles virus for efficacious treatment (29) Although this treatment is dependent on several variables, it is also modular in nature, and can be applied to alternative targeting and/or immunogenic peptides.

Treatment of vaccinated mice with H1299.3-targeted liposomes containing H250 resulted in a significant reduction in LLC1 subcutaneous tumor growth compared to H1299.3-targeted liposomes lacking H250. This is an aggressive cancer line indicating the strong potential of an efficacious therapy. Increased presence of CD8+ T cells in tumor section and ex vivo activation of CD8+ T cells using APCs from mice treated with H1299.3-targeted liposomes containing H250 implies that this treatment works by generating a cytotoxic T-cell response against the LLC1 tumor cells in vivo and is consistent with the in vitro murine and human data presented. Other CM therapies that generate Th1-like responses and increase levels of CD8+ infiltrates have demonstrated efficacy in both animal and human trials (4,6,7,30). Thus, the therapy presented here achieves similar beneficial immune activation in a safer and cost-effective manner compared to current CM therapies.

In conclusion, this study presents a novel cancer immunotherapy based on developing the minimal delivery platform to generate pseudoinfected cancer cells. We demonstrate proof of principle that a targeting liposome containing immunogenic peptide can facilitate presentation in HLA class 1 molecules, and that this treatment may be efficacious as a novel cancer immunotherapy.

REFERENCES

1. Ota, M O, Ndhlovu, Z, Oh, S, Piyasirisilp, S, Berzofsky, J A, Moss, W J et al. (2007). Hemagglutinin protein is a primary target of the measles virus-specific HLA-A2-restricted CD8+ T cell response during measles and after vaccination. J Infect Dis 195: 1799-1807.
2. Mellman, I, Coukos, G and Dranoff, G (2011). Cancer immunotherapy comes of age. Nature 480: 480-489.
3. Vitale, M, Cantoni, C, Pietra, G, Mingari, M C and Moretta, L (2014). Effect of tumor cells and tumor microenvironment on NK-cell function. Eur J Immunol 44: 158:2-1592.
4. Shiao, S L, Ganesan, A P, Rugo, H S and Coussens, L M (2011). Immune microenvironments in solid tumors: new targets for therapy. Genes Dev 25: 2559-2572.
5. Chiocca, E A and Rabkin, S D (2014). Oncolytic viruses and their application to cancer immunotherapy. Cancer Immunol Res 2: 295-300.
6. Dudley, M E, Wunderlich, J R, Robbins, P F, Yang, J C, Hwu, P, Schwartzentruber, D J et al. (2002). Cancer regression and autoimmunity in patients after clonal repopulation with antitumor lymphocytes. Science 298: 850-854.
7. Hamid, O, Robert, C, Daud, A, Hodi, F S, Hwu, W J, Kefford, R et al. (2013). Safety and tumor responses with lambrolizumab (anti-PD-1) in melanoma. N Engl J Med 369: 134-144.
8. Guillerme, J B, Boisgerault, N, Roulois, D, Ménager, J, Combredet, C, Tangy, F et al. (2013). Measles virus vaccine-infected tumor cells induce tumor antigen cross-presentation by human plasmacytoid dendritic cells. Clin Cancer Res 19: 1147-1158.
9. Dass, C R (2008). Drug delivery in cancer using liposomes. Methods Mol Biol 437: 177-182.
10. Umlauf, B J, Mercedes, J S, Chung, C Y and Brown, K C (2014). Identification of a novel lysosomal trafficking peptide using phage display biopanning coupled with endocytic selection pressure. Bioconjug Chem 25: 1829-1837.
11. van Endert, P M (1996). Peptide selection for presentation by HLA class I: a role for the human transporter associated with antigen processing? Immunol Res 15: 265-279.

12. Gray, B P, McGuire, M J and Brown, K C (2013). A liposomal drug platform overrides peptide ligand targeting to a cancer biomarker, irrespective of ligand affinity or density. PLoS One 8: e72938.
13. Taurin, S, Nehoff, H and Greish, K (2012). Anticancer nanomedicine and tumor vascular permeability; Where is the missing link? J Control Release 164: 265-275.
14. McGuire, M J, Gray, B P, Li, S, Cupka, D, Byers, L A, Wu, L et al. (2014). Identification and characterization of a suite of tumor targeting peptides for non-small cell lung cancer. Sci Rep 4: 4480.
15. Klionsky, D J (2007). Autophagy: from phenomenology to molecular understanding in less than a decade. Nat Rev Mol Cell Biol 8: 931-937.
16. Shah, J K, Garner, H R, White, M A, Shames, D S and Minna, J D (2007). sIR: siRNA Information Resource, a web-based tool for siRNA sequence design and analysis and an open access siRNA database. BMC Bioinformatics 8: 178.
17. Lee, R S, Tartour, E, van der Bruggen, P, Vantomme, V, Joyeux, I, Goud, B et al. (1998). Major histocompatibility complex class I presentation of exogenous soluble tumor antigen fused to the B-fragment of Shiga toxin. Eur I Immunol 28: 2726-2737.
18. Noakes, K L, Teisserenc, H T, Lord, J M, Dunbar, P R, Cerundolo, V and Roberts, L M (1999). Exploiting retrograde transport of Shiga-like toxin 1 for the delivery of exogenous antigens into the MHC class I presentation pathway. FEBS Lett 453: 95-99.
19. Haicheur, N, Bismuth, E, Bosset, S, Adotevi, O, Warnier, G, Lacabanne, V et al. (2000). The B subunit of Shiga toxin fused to a tumor antigen elicits CTL and targets dendritic cells to allow MHC class I-restricted presentation of peptides derived from exogenous antigens. J Immunol 165: 3301-3308.
20. Sandvig, K, Spilsberg, B, Lauvrak, S U, Torgersen, M L, Iversen, T G and van Deurs, B (2004). Pathways followed by protein toxins into cells. Int J Med Microbiol 293: 483-490.
21. Johannes, L and Römer, W (2010). Shiga toxins—from cell biology to biomedical applications. Nat Rev Microbiol 8: 105-116.
22. McEnaney, P J, Parker, C G, Zhang, A X and Spiegel, D A (2012). Antibody-recruiting molecules: an emerging paradigm for engaging immune function in treating human disease. ACS Chem Biol 7: 1139-1151.
23. Lu, Y and Low, P S (2002). Folate targeting of haptens to cancer cell surfaces mediates immunotherapy of syngeneic murine tumors. Cancer Immunol Immunother 51: 153-162.
24. Crotzer, V L and Blum, J S (2009). Autophagy and its role in MHC-mediated antigen presentation. J Immunol 182: 3335-3341.
25. Patterson, N L and Minters, J D (2012). Intersection of autophagy with pathways of antigen presentation. Protein Cell 3: 911-920.
26. Nixon, R A (2013). The role of autophagy in neurodegenerative disease. Nat Med 19: 983-997.
27. Sandvig, K and van Deurs, B (2002). Membrane traffic exploited by protein toxins. Annu Rev Cell Dev Biol 18: 1-24.
28. Ovsyannikova, I G, Johnson, K L, Bergen, H R 3rd and Poland, G A (2007). Mass spectrometry and peptide-based vaccine development. Clin Pharmacol Ther 82: 644-652.
29. Centers for Disease Control and Prevention (CDC) (2012). Vaccination coverage among children in kindergarten—United States, 2011—12 school year. MMWR Morb Mortal Wkly Rep 61: 647-652.
30. Bauzon, M and Hermiston, T (2014). Armed therapeutic viruses—a disruptive therapy on the horizon of cancer immunotherapy. Front Immunol 5: 74.
31. Schwendener, R A, Ludewig, B, Cerny, A and Engler, O (2010) Liposome-based vaccines. Methods Mol Biol 605: 163-175.
32. Umlauf, B J, Pinsky, N A, Ovsyannikova, I G and Poland, G A (2012). Detection of vaccinia virus-specific IFNγ and IL-10 secretion from human PBMCs and CD8+ T cells by ELISPOT. Methods Mol Biol 792: 199-218.
33. Fernandez-Viña, M A, Falco, M, Sun, Y and Stastny, P (1992). DNA typing for HLA class I alleles: I. Subsets of HLA-A2 and of -A28. Hum Immunol 33: 163-173.
34. Chung, C Y, Madhunapantula, S V, Desai, D, Amin, S and Robertson, G P (2011). Melanoma prevention using topical PRISe. Cancer Prev Res (Phila) 4: 935-948.
35. Feldman, J P, Goldwasser, R and Mark, S (2009). A mathematical model for tumor volume evaluation using two-dimensions. J Appl Quant 4: 455-462.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A minimal antigen delivery system consisting essentially of PEGylated stealth liposomes loaded with an immunogenic human leukocyte antigen (HLA) class I restricted peptide and surface-modified with a cancer-specific cell targeting peptide which mediates binding and internalization of the liposomes into a target cell, wherein the HLA class I restricted peptide is a vaccine-dependent, secondary immunogenic HLA class I restricted peptide.

2. The system of claim 1, wherein the antigen is a vaccine-dependent, secondary immunogenic HLA class I restricted peptide, that is measles virus hemagglutinin peptide H250.

3. The system of claim 1, wherein the antigen is a vaccine-dependent, secondary immunogenic HLA class I restricted peptide, that is smallpox virus H-2Kd-restricted vaccinia-specific peptide, A5275-83 (VACV-A52).

4. The system of claim 1, wherein the cell-targeting peptide is H1299.3.

5. The system of claim 2, wherein the cell-targeting peptide is H1299.3.

6. The system of claim 3, wherein the cell-targeting peptide is H1299.3.

7. The system of claim 1 that does not comprise any viral particles, toxins, or biologically-derived material.

8. A method of making an antigen delivery system of claim 1, comprising the step(s) of: surface modifying the PEGylated stealth liposomes loaded with the HLA class I restricted peptide by conjugating to the surface the cell targeting peptide.

9. A method of making an antigen delivery system of claim 1, comprising the step(s) of:
   loading the PEGylated stealth liposomes by forming the liposomes in the presence of the class restricted peptide; and surface modifying the PEGylated stealth liposomes loaded with the HLA class I restricted peptide by conjugating to the surface the cell targeting peptide.

10. A method of using the antigen delivery system of claim 1, comprising the step(s) of: introducing the antigen delivery system into a host in need thereof.

11. A method of using the antigen delivery system of claim 1, comprising the step(s) of: introducing the antigen delivery system into a person in need thereof, and detecting a resultant secondary immune response or inhibition of the target cell.

12. A method of using the antigen delivery system of claim 2, comprising the step(s) of: introducing the antigen delivery system into a person in need thereof, and detecting a resultant secondary immune response or inhibition of the target cell.

13. A method of using the antigen delivery system of claim 3, comprising the step(s) of: introducing the antigen delivery system into a person in need thereof, and detecting a resultant secondary immune response or inhibition of the target cell.

14. A method of using the antigen delivery system of claim 4, comprising the step(s) of: introducing the antigen delivery system into a person in need thereof, and detecting a resultant secondary immune response or inhibition of the target cell.

15. A method of using the antigen delivery system of claim 5, comprising the step(s) of: introducing the antigen delivery system into a person in need thereof, and detecting a resultant secondary immune response or inhibition of the target cell.

16. A method of using the antigen delivery system of claim 6, comprising the step(s) of: introducing the antigen delivery system into a person in need thereof, and detecting a resultant secondary immune response or inhibition of the target cell.

* * * * *